(12) United States Patent
Yarborough et al.

(10) Patent No.: US 6,626,870 B1
(45) Date of Patent: Sep. 30, 2003

(54) STOPPERING METHOD TO MAINTAIN STERILITY

(75) Inventors: Cody L Yarborough, Ft. Collins, CO (US); Michael R. Duncan, Ft. Collins, CO (US); Richard L. Norton, Ft. Collins, CO (US); Rajan Bawa, Ft. Collins, CO (US); Dominic G. Madril, Loveland, CO (US); Christopher J. Barrett, Ft. Collins, CO (US)

(73) Assignee: Artix Laboratories, Inc., Fort Collins, CO (US)

( * ) Notice: Subject to any disclaimer, the term of this patent is extended or adjusted under 35 U.S.C. 154(b) by 0 days.

(21) Appl. No.: 09/536,479

(22) Filed: Mar. 27, 2000

(51) Int. Cl.⁷ .................................................. A61M 5/32
(52) U.S. Cl. ........................ 604/199; 604/187; 604/194
(58) Field of Search ................................ 604/199, 187, 604/196, 194, 221, 218

(56) References Cited

U.S. PATENT DOCUMENTS

| | | | |
|---|---|---|---|
| 2,353,986 A | 7/1944 | Barr | 34/5 |
| 2,549,417 A * | 4/1951 | Brown | 604/90 |

(List continued on next page.)

FOREIGN PATENT DOCUMENTS

| | | | |
|---|---|---|---|
| CA | 2254361 | 5/1999 | A61M/5/31 |
| DE | 3311525 | 10/1984 | F26B/5/06 |
| DE | 19702564 | 9/1998 | F25D/3/10 |
| DE | 19751226 | 1/1999 | B65B/3/04 |
| EP | 0242956 A1 * | 10/1987 | |
| EP | 0430474 | 6/1991 | A61K/9/70 |
| EP | 0539751 | 5/1993 | A61K/9/00 |
| EP | 0743072 | 11/1996 | A61M/5/315 |
| FR | 1109316 | 1/1956 | 19/4 |
| JP | 5-504941 | 7/1993 | A61K/6/00 |
| JP | 6-196132 | 7/1994 | H01J/65/04 |
| WO | 91/01126 | 2/1991 | A61K/6/00 |
| WO | 97/11155 | 3/1997 | C12M/1/00 |

OTHER PUBLICATIONS

US Patent Applicant Publication, US2001/0042317 A1, Pub date: Nov. 22, 2001, entire document.*
"Lyophilization", *McGraw–Hill Concise Encyclopedia of Science & Technology, Fourth Edition*, Sybil P. Parker, Editor in Chief, p. 1128, (1998).

Primary Examiner—Gregory Huson
Assistant Examiner—Khoa Huynh
(74) Attorney, Agent, or Firm—Schwegman, Lundberg, Woessner & Kluth, P.A.

(57) ABSTRACT

A syringe assembly is provided which includes a hollow barrel that has an interior wall. The interior wall defines a chamber that retains medication. The hollow barrel also includes a distal end and a proximal end. The distal end of the hollow barrel has a passageway that is in contact with the chamber. The proximal end of the hollow barrel has an aperture. The syringe assembly also includes a primary plunger tip that is slidably positioned, in fluid tight engagement, with the interior wall. The primary plunger tip has a receptor to engage an engager of an elongated tip plunger rod. The syringe assembly also includes a secondary plunger tip that is slidably positioned, in fluid tight engagement, with the interior wall. The secondary plunger tip also has a receptor to engage an engager of a tip plunger rod. The secondary plunger tip is disposed between the primary plunger tip and the proximal end of the hollow barrel. The syringe assembly also includes a tip plunger rod, which facilitates operation of the secondary plunger tip, engaged to the secondary plunger tip. The present invention also provides a process for providing a lyophilized medication (i.e., lyophilizate) in a syringe assembly and also provides a process for reconstituting a medication in a syringe assembly.

36 Claims, 8 Drawing Sheets

U.S. PATENT DOCUMENTS

| | | | | |
|---|---|---|---|---|
| 3,477,431 A | * | 11/1969 | Walecka | 604/89 |
| 4,030,498 A | | 6/1977 | Tompkins | 128/218 P |
| 4,040,421 A | | 8/1977 | Young | 128/218 N |
| 4,127,127 A | | 11/1978 | Wong et al. | 128/260 |
| 4,188,949 A | * | 2/1980 | Antoshkiw | 604/199 |
| 4,240,426 A | | 12/1980 | Akhavi | 128/218 N |
| 4,286,389 A | | 9/1981 | Ogle | 34/5 |
| 4,439,420 A | | 3/1984 | Mattei et al. | 424/78 |
| 4,443,430 A | | 4/1984 | Mattei et al. | 424/78 |
| 4,452,473 A | | 6/1984 | Ruschke | 285/81 |
| 4,501,719 A | | 2/1985 | Williams | 422/102 |
| 4,631,055 A | | 12/1986 | Redl et al. | 604/82 |
| 4,673,396 A | * | 6/1987 | Urbaniak | |
| 4,729,208 A | | 3/1988 | Galy et al. | 53/432 |
| 4,743,229 A | | 5/1988 | Chu | 604/82 |
| 4,758,230 A | | 7/1988 | Rycroft | 604/118 |
| 4,766,908 A | * | 8/1988 | Clement | |
| 4,938,763 A | | 7/1990 | Dunn et al. | 604/891.1 |
| 4,978,336 A | | 12/1990 | Capozzi et al. | 604/82 |
| 4,981,696 A | | 1/1991 | Loomis et al. | 424/486 |
| 4,994,029 A | | 2/1991 | Rohrbough | 604/82 |
| 5,007,940 A | | 4/1991 | Berg | 623/66 |
| 5,116,315 A | | 5/1992 | Capozzi et al. | 604/82 |
| 5,234,529 A | | 8/1993 | Johnson | 156/345 |
| 5,278,201 A | | 1/1994 | Dunn et al. | 523/113 |
| 5,324,519 A | | 6/1994 | Dunn et al. | 424/426 |
| 5,487,897 A | | 1/1996 | Polson et al. | 424/426 |
| 5,489,266 A | * | 2/1996 | Grimard | 604/218 |
| 5,556,279 A | | 9/1996 | Wolf et al. | 433/82 |
| 5,566,729 A | | 10/1996 | Grabenkort et al. | 141/25 |
| 5,599,552 A | | 2/1997 | Dunn et al. | 424/423 |
| 5,637,100 A | * | 6/1997 | Sudo | 604/218 |
| 5,660,849 A | | 8/1997 | Polson et al. | 424/426 |
| 5,702,716 A | | 12/1997 | Dunn et al. | 424/422 |
| 5,779,668 A | * | 7/1998 | Grabenkort | 604/218 |
| 5,788,670 A | * | 8/1998 | Reinhard et al. | 604/191 |
| 5,893,842 A | | 4/1999 | Imbert | 604/110 |
| 5,908,054 A | | 6/1999 | Safabash et al. | 141/26 |
| 5,928,215 A | | 7/1999 | Caizza et al. | 604/411 |
| 5,947,933 A | | 9/1999 | Reichenbach et al. | 604/198 |
| 5,951,160 A | | 9/1999 | Ronk | 366/130 |
| 5,957,166 A | | 9/1999 | Safabash | 141/26 |
| 6,071,530 A | | 6/2000 | Polson et al. | 424/426 |
| 6,090,092 A | | 7/2000 | Fowles et al. | 604/413 |
| 6,106,502 A | | 8/2000 | Richmond | 604/246 |
| 6,106,783 A | | 8/2000 | Gamble | 422/102 |
| 6,136,273 A | | 10/2000 | Seguin et al. | 422/99 |
| 6,139,530 A | * | 10/2000 | Hiejima et al. | 604/218 |
| 6,143,276 A | | 11/2000 | Unger | |
| 6,174,304 B1 | | 1/2001 | Weston | |
| 6,197,194 B1 | | 3/2001 | Whitmore | |
| 6,223,786 B1 | | 5/2001 | Castellano | |
| 6,290,680 B1 | * | 9/2001 | Forsberg et al. | |
| 6,302,160 B2 | | 10/2001 | Castellano | |
| 6,364,865 B1 | * | 4/2002 | Lavi et al. | |

* cited by examiner

STOPPERING METHOD TO MAINTAIN STERILITY

BACKGROUND OF THE INVENTION

Organic compounds, and more specifically pharmaceuticals, are generally more stable when they exist as a solid or powder than when they exist in solution. As such, the shelf-life of a pharmaceutical stored in solution is generally shorter than the shelf-life of the pharmaceutical stored as a solid or powder. Since many pharmaceuticals are stored for extended periods of time before use, it is advantageous to have these pharmaceuticals remain active over the extended period of time. It is therefore desirable to store pharmaceuticals, over an extended period of time, as a solid or powder. This especially includes those pharmaceuticals that are ultimately reconstituted before being administered as a solution.

Lyophilization is routinely used in the preparation and storage of pharmaceuticals. In such applications, lyophilization is usually carried out by freezing a solution containing the pharmaceutical, followed by sublimation to provide the solid or powder essentially free of solvent. Lyophilization directly in a vial or ampule requires transfer of the reconstituted pharmaceutical from the vial or ampule to a syringe. As such, a syringe is especially useful for the lyophilization of an injectable medication since the medication is ultimately administered from the syringe. Lyophilization can be performed wherein a solution containing the pharmaceutical is lyophilized directly in a syringe. See, U.S. application Ser. No. 09/190,341. The lyophilized pharmaceutical (i.e., medication) can then be stored in the syringe wherein a diluent can be added to the syringe for reconstitution of the medication just prior to administration. The reconstituted medication can then be administered directly to the patient from the same hypodermic syringe in which the lyophilized medication had been stored.

Several problems exist in the packaging, shipment, and storage of a lyophilized pharmaceutical. Syringes are usually provided in an individual sterile package which is opened at the time of use. However, non-sterile matter (e.g., bacteria) from the environment may enter the syringe barrel through the proximal open end when the syringe is packaged. The pharmaceutical is displaced between the distal end of the syringe barrel, which is sealed, and the plunger tip, which creates a seal. As such, the pharmaceutical is usually contained within a sterile portion of the syringe barrel. The portion of the syringe barrel between the plunger tip and the proximal end, however, is open to the environment. Even though the syringe may be packaged in a sterile packaging system, non-sterile matter (e.g., bacteria) can be introduced in that portion of the syringe barrel during packaging and can survive (i.e., remain dormant) in the syringe barrel over the lengthy storage time.

Reconstitution of the lyophilized pharmaceutical can be accompanied by the entrance of any non-sterile matter (e.g., bacteria) present in the non-sterile portion of the chamber of the syringe barrel. This occurs because the plunger rod and the stopper may be drawn back and forth along the portion of the syringe barrel where non sterile matter was introduced. Each cycling of the stopper along the barrel provides potential for contamination of the contents contained within the syringe. The introduction of non-sterile matter (e.g., bacteria) into the chamber of the syringe barrel results in the syringe, and the lyophilized pharmaceutical contained therein, being discarded or recycled, or infecting the patient. The likelihood of the entrance of non-sterile matter is heightened when the reconstitution is accompanied by syringe-to-syringe mixing.

Because of the extremely high requirements for sterility and quality control, lyophilization of pharmaceuticals is a very expensive process. The process requires a significant amount of energy to sustain the proper freezing and vacuum conditions in a lyophilization chamber. It is also costly and time consuming to discard or recycle those syringes, and the lyophilized pharmaceutical contained therein, because of contamination. Moreover, serious medical risks exist when a medication that is not sterile is parentally administered to a patient. As such, a syringe assembly is needed that will maintain the sterility of the lyophilized product during packaging, shipment and storage.

SUMMARY OF THE INVENTION

The present invention is directed to a syringe assembly that maintains sterility, as well as to processes for their filling and use. The first syringe assembly includes a hollow barrel that has an interior wall. The interior wall defines a chamber that retains medication. The hollow barrel also includes a distal end and a proximal end. The distal end of the hollow barrel has a passageway that is in contact with the chamber. The proximal end of the hollow barrel has an aperture. The syringe assembly also includes a primary plunger tip that is slidably positioned, in fluid tight engagement, with the interior wall. The primary plunger tip has a receptor to engage an engager of an elongated tip plunger rod. The syringe assembly also includes a secondary plunger tip that is slidably positioned, in fluid tight engagement, with the interior wall. The secondary plunger tip also has a receptor to engage an engager of a tip plunger rod. The secondary plunger tip is disposed between the primary plunger tip and the proximal end of the hollow barrel. The syringe assembly also includes a tip plunger rod, which facilitates operation of the secondary plunger tip, engaged to the secondary plunger tip.

The second syringe assembly is similar to the first syringe assembly but further includes an elongated tip plunger rod with an engager that is configured to engage the receptor of the primary plunger tip. The elongated tip plunger rod facilitates the operation of the primary plunger tip. The third syringe assembly is the first syringe assembly further including a medication disposed between the primary plunger tip and the distal end of the hollow barrel.

The present invention also provides a process for providing a lyophilized medication (i.e., lyophilizate) in a syringe assembly. The process includes providing a third syringe assembly and lyophilizing the solution in the chamber to provide a lyophilizate. The process also includes inserting the primary plunger tip that is slidably positioned, in fluid tight engagement, with the interior wall. The primary plunger tip has a receptor to engage an engager of an elongated tip plunger rod. The primary plunger tip is disposed between the lyophilizate and the proximal end of the hollow barrel. The process also includes inserting a secondary plunger tip that is slidably positioned, in fluid tight engagement, with the interior wall. The secondary plunger tip is engaged to a tip plunger rod. The secondary plunger tip is disposed between the primary plunger tip and the proximal end of the hollow barrel.

The present invention also provides a process for reconstituting a medication in a syringe assembly. The process includes providing a second syringe assembly. The second syringe assembly also includes a medication that is disposed between the primary plunger tip and the distal end of the hollow barrel. The second syringe assembly also includes a discharge assembly or cannula (e.g., a needle) in fluid transport connection with the passageway. The secondary plunger tip is disposed between the primary plunger tip and the proximal end of the hollow barrel. The process also includes removing the secondary plunger tip from the hollow barrel and placing the discharge assembly in contact with a diluent. The process also includes urging the primary plunger tip proximally and away from the distal end of the hollow barrel. As the primary plunger is urged away from the distal end of the hollow barrel, the diluent is urged through the discharge assembly and through the distal end of the hollow barrel. As such, the diluent comes into contact with the medication thereby effectively reconstituting the medication. Alternatively, the distal end of a second syringe assembly can be connected to a third syringe containing a diluent by means of a luer-lock coupler and the diluent can be discharged into the second syringe where it comes in contact with the medication. The mixture of diluent and medication can then be pushed back and forth between the two syringes until the contents are thoroughly mixed. The contents can then be drawn into one of the syringes, the coupler and other syringe can be removed, and a discharge assembly or cannula (e.g., a needle) can be attached to the syringe with the contents.

DETAILED DESCRIPTION OF THE INVENTION

Figure 1:
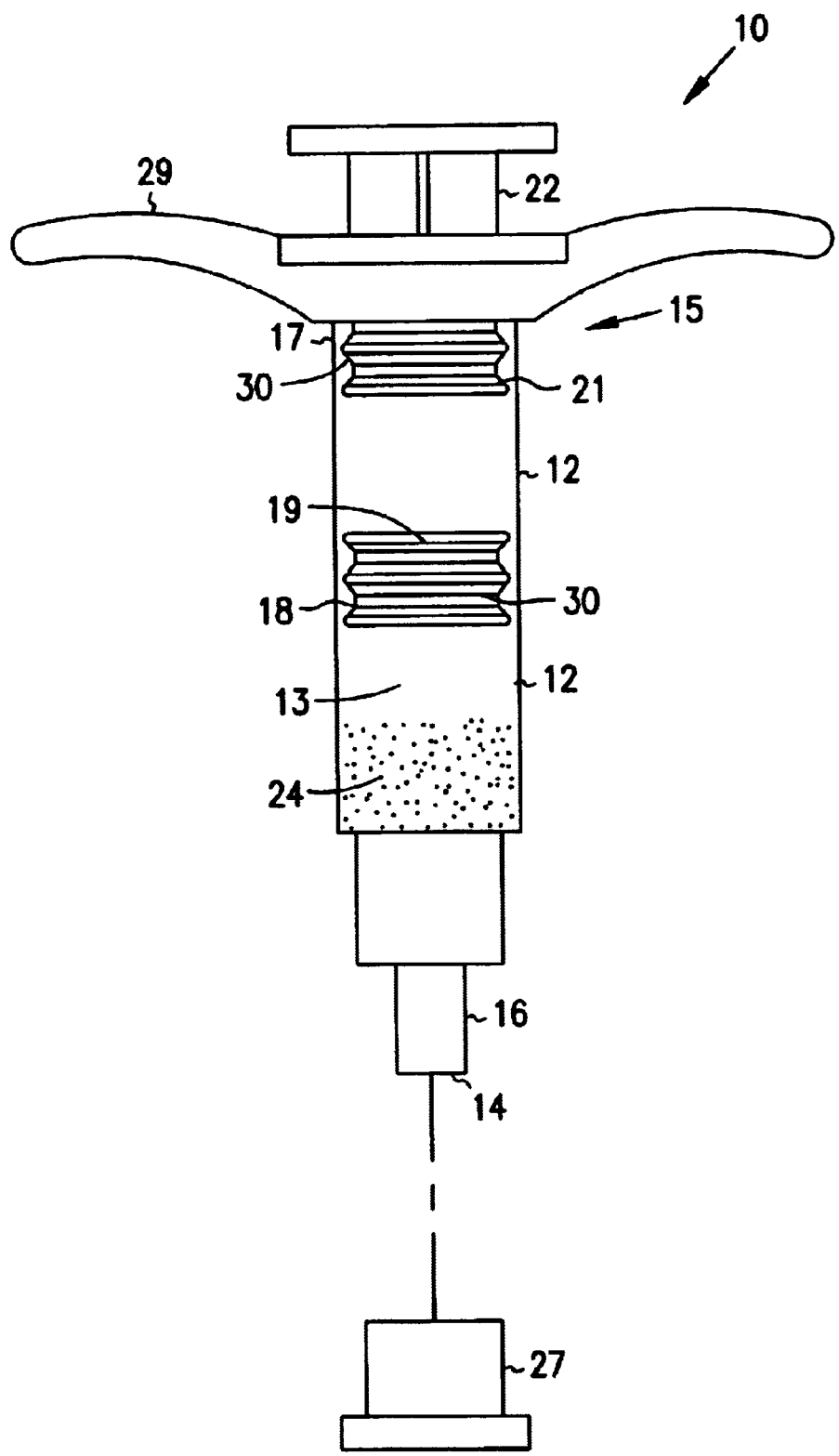
FIG. 1 is an illustration of a syringe assembly.

A syringe assembly in accordance with the subject invention is identified generally by the numeral 10 in FIG. 1. Syringe assembly 10 includes a hollow barrel 11 having an open proximal end 15, a distal end 14, and a substantially cylindrical interior wall 12 extending therebetween. The cylindrical interior wall 12 has a uniform circularity shaped cross section without any deformation in the side wall which will allow the primary plunger tip 18 and the secondary plunger tip 21 to maintain a fluid tight engagement with the cylindrical interior wall 12. Interior wall 12 defines a substantially cylindrical fluid receiving chamber 13. Distal end 14 of hollow barrel 11 includes a passageway 16 extending axially therethrough and communicating with chamber 13. Distal end 14 of hollow barrel 11 is configured to engage a sealing cap 27. In addition, distal end 14 of hollow barrel 11 is configured to engage a discharge assembly. The primary plunger tip 18 has a receptor 19 to engage an engager 28 of an elongated tip plunger rod 20 (see FIGS. 3–6). The secondary plunger tip 21 has a receptor 23 to engage an engager 31 of a tip plunger rod 22 (see FIGS. 7–10). The secondary plunger tip 21 is disposed between the primary plunger tip 18 and the proximal end 15 of the hollow barrel 11. Tip plunger rod 22 can be engaged to the secondary plunger tip 21 to facilitate operation of the secondary plunger tip 21.

The syringe assembly 10 can further include a discharge assembly. Specifically, the discharge assembly can include a needle 25 or a flexible cannula (not shown). The needle 25 can include an engager 50. The engager 50 of the needle 25 is configured to engage the locking luer type collar 33 on the distal end 14 of the hollow barrel 11. Needle 25 includes an elongate hollow tube 51 having a proximal end 52, a distal end 53 and a lumen 54 extending therebetween. Proximal end 52 of elongated hollow tube 51 is securely and substantially permanently mounted to a mounting hub 55 which is configured for threaded engagement with locking luer type collar 33 and distal end 14 of hollow barrel 11. The hollow barrel 11 can include a locking luer type collar 33 on the distal end 14. The discharge assembly can engage the locking luer type collar 33 on the distal end 14 of the hollow barrel 11.

Figure 2:
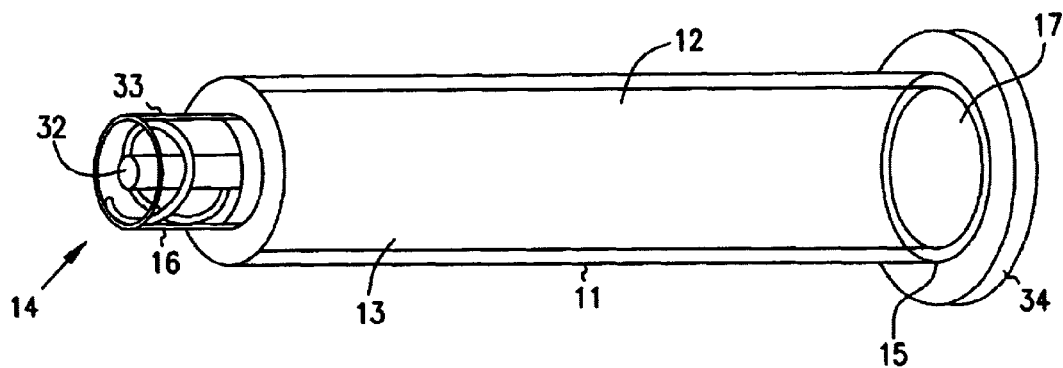
FIG. 2 is an illustration of a hollow barrel.
Figure 3:
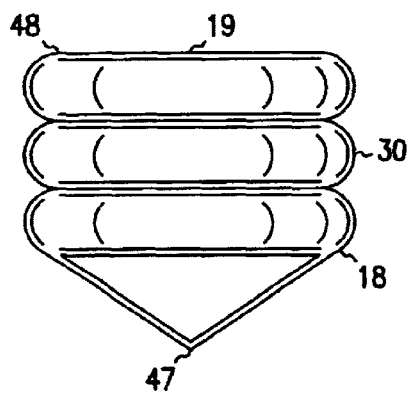
FIG. 3 is an illustration of a primary plunger tip.
Figure 4:
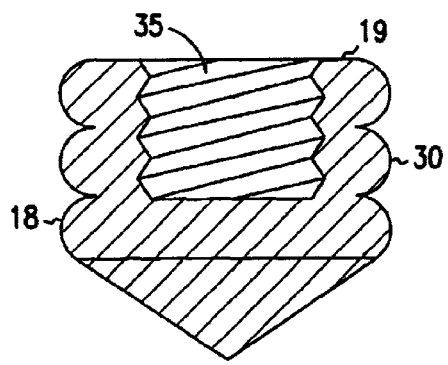
FIG. 4 is partial, cut-away side-view of a primary plunger tip.

The syringe assembly 10 can further include a sealing cap 27. The sealing cap seals the hollow barrel from contamination. The sealing cap 27 can be inserted over tip 32 of hollow barrel 11 (see FIG. 2). The sealing cap 27 can engage the locking luer type collar 33 on the distal end 14 of the hollow barrel 11.

The syringe assembly 10 can further include a flange 34 on the proximal end 15 of the hollow barrel 11. In addition, a flange extender 29 can be mounted on the hollow barrel 11 such that the flange extender 29 is in continuous contact with the flange 34. The flange extender 29 can project radially outward from the proximal end 15 of the hollow barrel 11 of the syringe assembly 10. The flange extender 29 can be permanently mounted on the hollow barrel 11 or the flange extender 29 can be removably mounted on the hollow barrel 11.

The hollow barrel 11 can be manufactured from any suitable material. Specifically, the hollow barrel 11 can be manufactured from glass and plastic (e.g., polypropylene, polyethylene, polycarbonate, polystyrene, and the like). The hollow barrel 11 can be sterilized. The hollow barrel 11 can be sterilized by any suitable means. More specifically, the hollow barrel 11 can be sterilized by gamma irradiation. The sterilization can occur after the medication 24 is introduced into the chamber 13 of the hollow barrel 11. Alternatively, sterilization can occur before the medication 24 is introduced into the chamber 13 of the hollow barrel 11. The size of the hollow barrel 11 can be any suitable size. Suitable sizes include a hollow barrel 11 of about 0.01 to about 50 cc, about 0.1 cc to about 25 cc, about 0.1 cc to about 10 cc, or about 0.5 cc to about 5 cc. The hollow barrel 11 can be manufactured by any suitable process. The hollow barrel 11 can be manufactured by an injecting molding process where the entire hollow barrel 11 is made as one unit.

The primary plunger tip 18 includes opposed proximal and distal ends 47 and 48. The primary plunger tip 18 is slidably positioned in fluid tight engagement with the cylindrical interior wall 12 (see FIG. 1). The primary plunger tip 18 can include a plurality of annular ribs 30 dimensioned for maintaining a fluid-tight engagement, while sliding, with the interior wall 12 (see FIGS. 1, 3–4, and 6). Specifically, the primary plunger tip 18 can include 2, 3, 4, or 5 annular ribs 30. More specifically the primary plunger tip 18 can include 3 or 4 annular ribs 30. Preferably the annular ribs are configured to provide fluid-tight engagement for movement of the primary plunger tip 18 in both directions, i.e., pushing tip 18 toward the distal end 14 and pulling tip 18 away from distal end 14.

Figure 5:
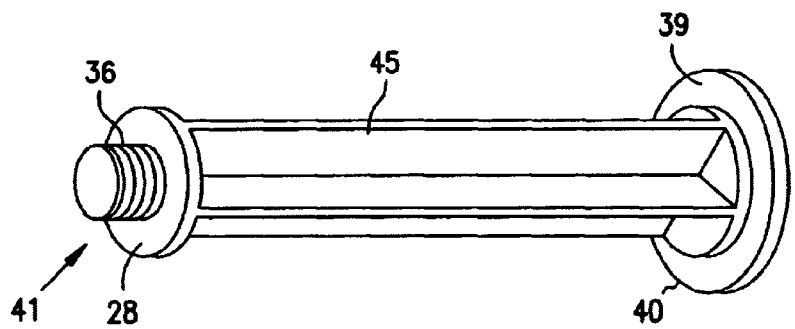
FIG. 5 is an illustration of a an elongated tip plunger rod.
Figure 6:
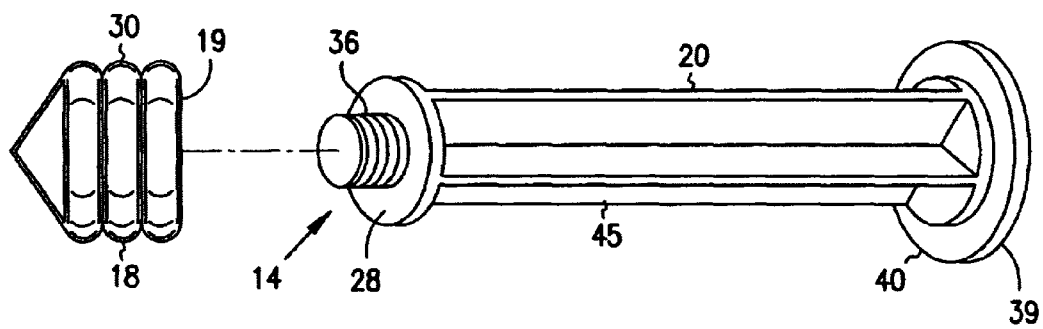
FIG. 6 is an illustration of a primary plunger tip engaged to an elongated tip plunger rod.
Figure 7:
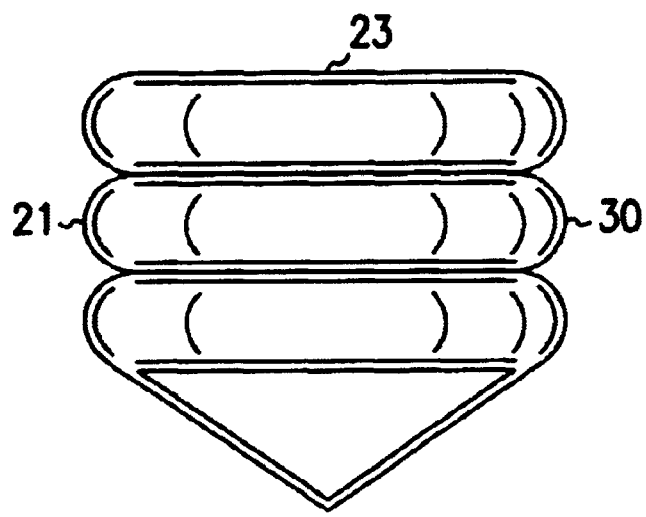
FIG. 7 is an illustration of a secondary plunger tip.
Figure 8:
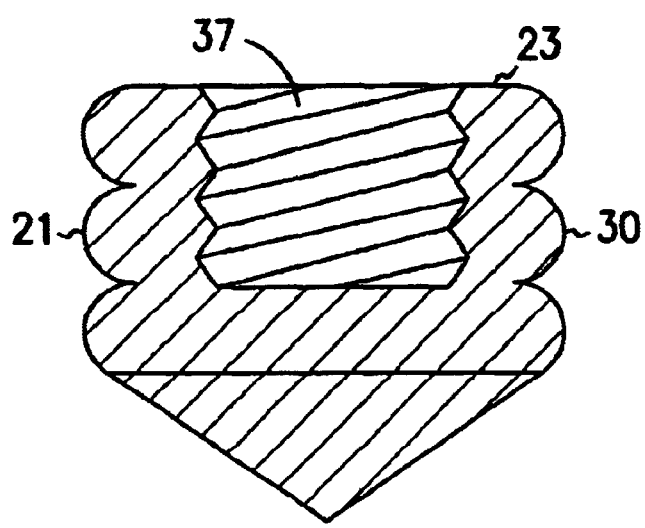
FIG. 8 is a partial, cut-away side-view of a secondary plunger tip.
Figure 9:
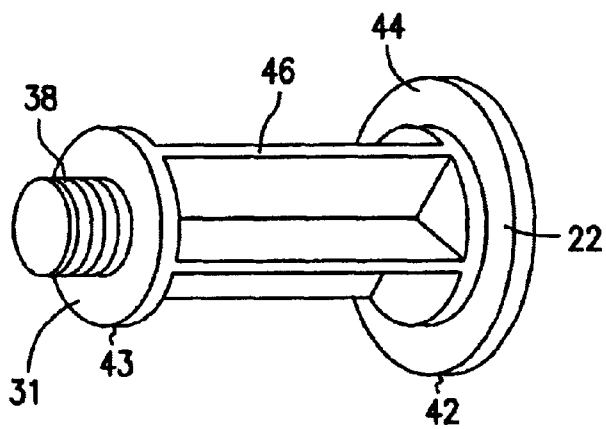
FIG. 9 is an illustration of a tip plunger rod.
Figure 10:
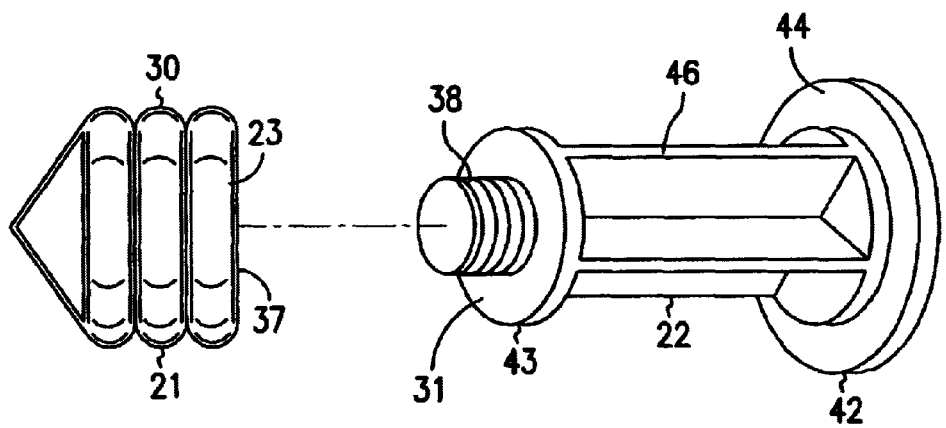
FIG. 10 is an illustration of a secondary plunger tip engaged to a tip plunger rod.
Figure 11:
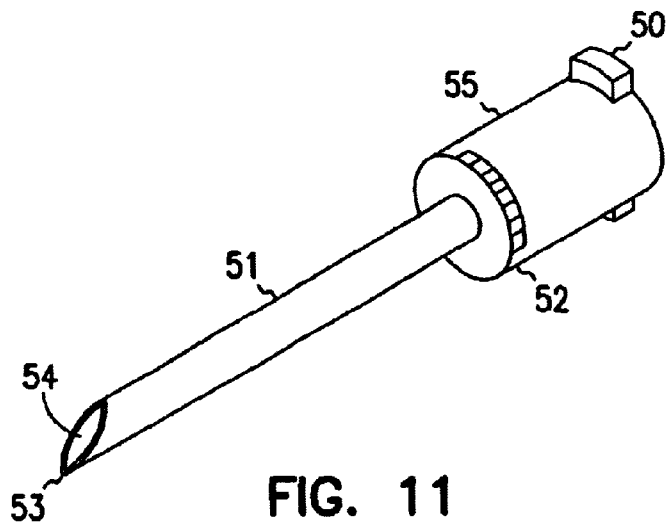
FIG. 11 is an illustration of a needle.
Figure 12A:
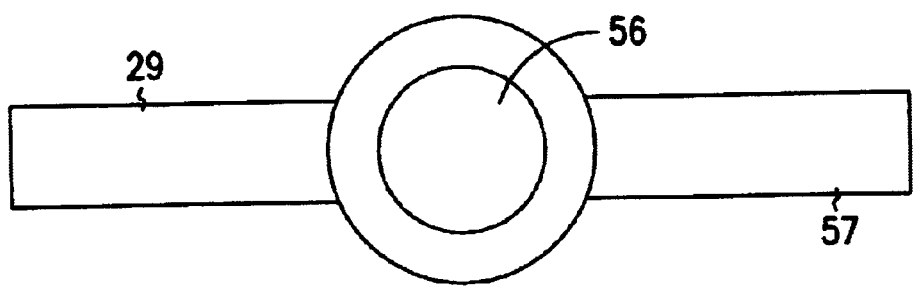
FIG. 12A is a top view of a flange extender.
Figure 12B:
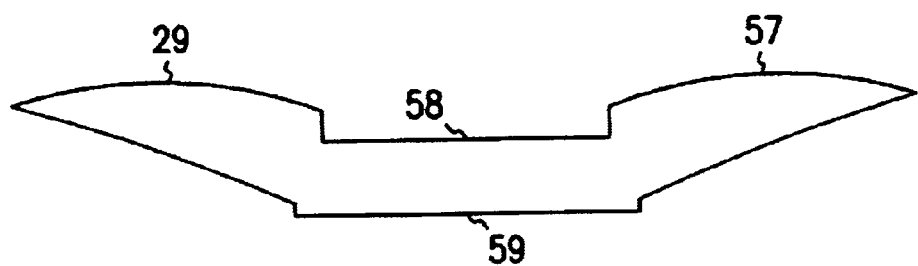
FIG. 12B is a side view of a flange extender.
Figure 13:
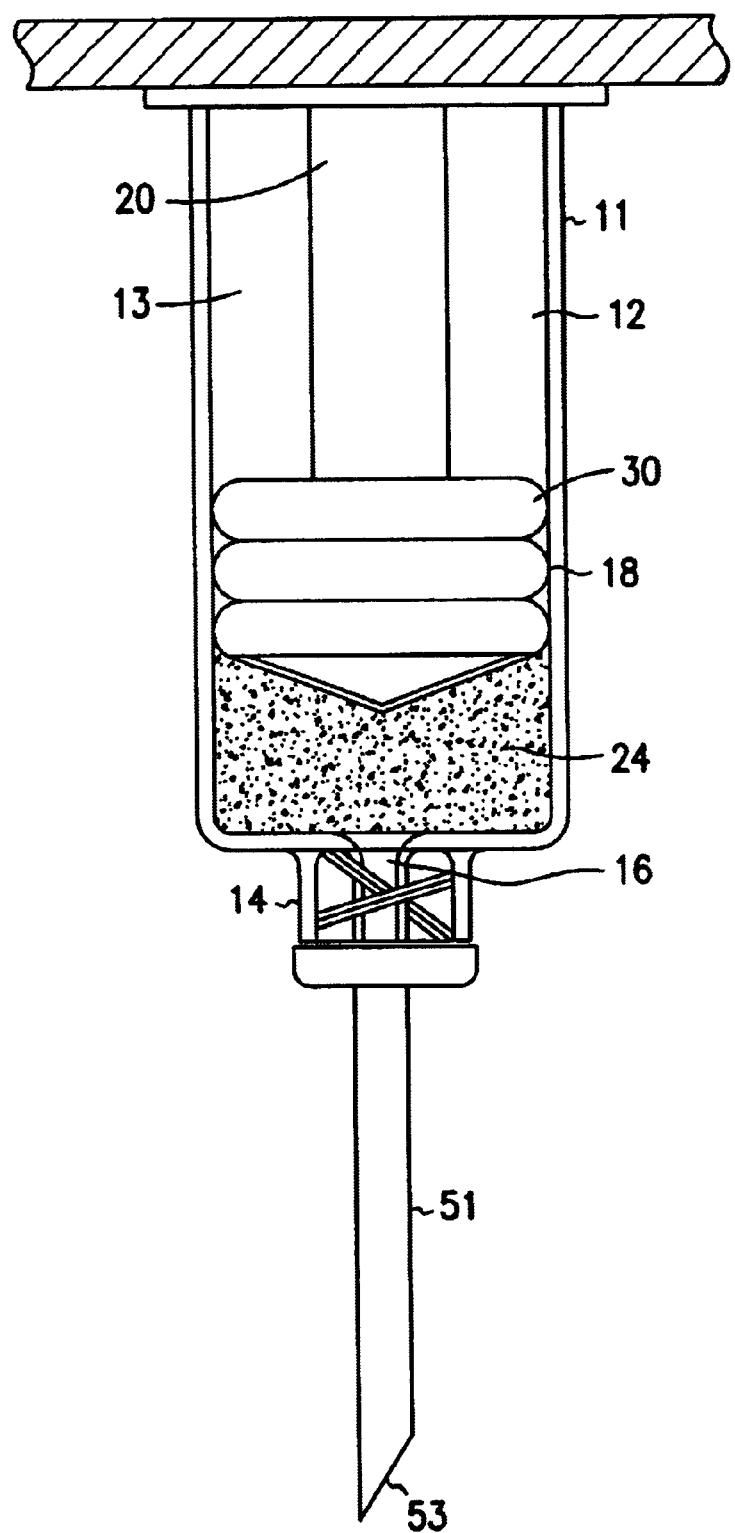
FIG. 13 is a partial view of a syringe assembly containing medication and a needle.
Figure 14:
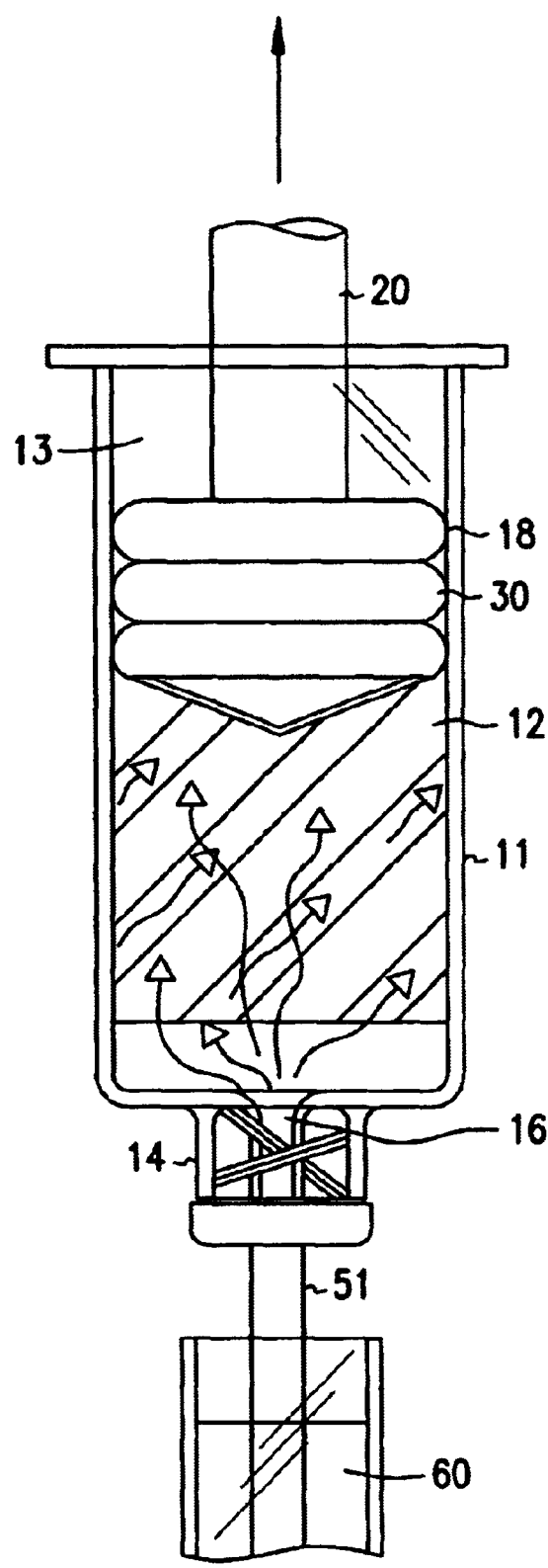
FIG. 14 is a partial view of a medication being reconstituted in a syringe assembly.

The syringe assembly 10 can include an elongated tip plunger rod 20 (see FIGS. 5–6). The elongated tip plunger rod 20 includes an engager 28. Specifically, the engager 28 can be a threaded end 36. The primary plunger tip 18 includes a receptor 19 to engage an engager 28 of an elongated tip plunger rod 20 (see FIGS. 1 and 3–6). Specifically, the engager 28 can be a threaded end 36 and the receptor 19 can be a threaded receiving end 35 (see FIGS. 4–6). When the engager 28 is a threaded end 36 and when the receptor 19 is a threaded receiving end 35, the elongated tip plunger rod 20 can be engaged to the primary plunger tip 18 by screwing the threaded end 36 into the threaded receiving end 35 (see FIG. 6).

The primary plunger tip 18 can have any suitable shape, provided the primary plunger tip 18 maintains fluid tight engagement with the interior wall 12 of the hollow barrel 11. The distal end 47 of the primary plunger tip 18 can be shaped to facilitate the egress of the diluent 60 and medication 24 from chamber 13 of the hollow barrel 11. Specifically, the cross-sectional shape of the distal end 47 of the primary plunger tip 18 can be v-shaped. The primary plunger tip 18 can be manufactured from any suitable material. Suitable materials include plastic (e.g., polypropylene, polyethylene, polycarbonate, polystyrene, and the like), rubber (e.g., natural rubber or synthetic rubber), thermoplastic elastomers, or any combination thereof. The primary plunger tip 18 can be sterilized. The primary plunger tip 18 can be sterilized by any suitable means. More specifically, the primary plunger tip 18 can be sterilized by gamma irradiation. The sterilization can occur after the medication 24 is introduced into the chamber 13 of the hollow barrel 11. Alternatively, sterilization can occur after the medication 24 is introduced into the chamber 13 of the hollow barrel 11.

The elongated tip plunger rod 20 includes a proximal end 40, a distal end 41 and a body 45 extending therebetween. The proximal end 40 includes a flange 39. The distal end 41 includes an engager 28. The length of the elongated tip plunger rod 20 (i.e., the body 45) is sufficiently long as to enable the engager 28 of the elongated tip plunger rod 20 to engage the receptor 19 of the primary plunger tip 18, even when the primary plunger tip 18 is located at the distal end 14 of the chamber 13 of the hollow barrel 11.

The elongated tip plunger rod 20 can be manufactured from any suitable material. Specifically, the elongated tip plunger rod 20 can be manufactured from glass and plastic (e.g., polypropylene, polyethylene, polycarbonate, polystyrene, and the like). The elongated tip plunger rod 20 can be sterilized. The elongated tip plunger rod 20 can be sterilized by any suitable means. More specifically, the elongated tip plunger rod 20 can be sterilized by gamma irradiation. The sterilization can occur before the medication 24 is introduced into the chamber 13 of the hollow barrel 11 Alternatively, sterilization can occur after the medication 24 is introduced into the chamber 13 of the hollow barrel 11.

The secondary plunger tip 21 is slidably positioned in fluid tight engagement inside the interior wall 12 of the hollow barrel 11 (see FIG. 1). The secondary plunger tip 21 can include a plurality of annular ribs 30 dimensioned for maintaining fluid-tight engagement, while sliding, with the interior wall 12 of the hollow barrel 11 (see FIGS. 1, 7–8, and 10). Specifically, the secondary plunger tip 21 can include 2, 3, 4, or 5 annular ribs 30. More specifically, the secondary plunger tip 21 can include 3 or 4 annular ribs 30.

The secondary plunger tip 21 includes a receptor 23 to engage the engager 31 of the tip plunger rod 22. Specifically, the receptor 23 can be a threaded receiving end 37. The tip plunger rod 22 includes an engager 31. Specifically, the engager 31 of the tip plunger rod 22 can be a threaded end 38 (see FIGS. 9–10). When the engager 31 is a threaded end 38 and when the receptor 23 is a threaded receiving end 37, the tip plunger rod 22 can be engaged to the secondary plunger tip 21 by screwing the threaded end 38 into the threaded receiving end 37 (see FIG. 10).

The secondary plunger tip 21 can be manufactured from any suitable material. Suitable materials include plastic (e.g., polypropylene, polyethylene, polycarbonate, polystyrene, and the like), rubber (e.g., natural rubber or synthetic rubber), thermoplastic elastomers, or any combination thereof. The secondary plunger tip 21 can be sterilized. The secondary plunger tip 21 can be sterilized by any suitable means. More specifically, the secondary plunger tip 21 can be sterilized by gamma irradiation. The sterilization can occur before the medication 24 is introduced into the chamber 13 of the hollow barrel 11. Alternatively, sterilization can occur after the medication 24 is introduced into the chamber 13 of the hollow barrel 11.

The tip plunger rod 22 includes a proximal end 42, a distal end 43 and a body 46 extending therebetween. The proximal end 42 can include a flange 44. The distal end 43 can include an engager 31. The length of the tip plunger rod 22 (i.e., the body 46) can be sufficiently short such that when the receptor 23 of the secondary plunger tip 21 is engaged to the engager 31 of the tip plunger rod 22, the secondary plunger tip 21 is located at the proximal end 15 of the chamber 13 of the hollow barrel 11. The location of the secondary plunger tip 21 at the proximal end 15 of the chamber 13 of the hollow barrel 11 will ensure that the portion of interior wall 12, and the contents thereof, located between the secondary plunger tip 21 and the primary plunger tip 18 will remain sterile during the packaging, shipping and storage of the syringe assembly 10.

The location of the secondary plunger tip 21 at the proximal end 15 of the chamber 13 of the hollow barrel 11 can prevent the user from discarding the elongated tip plunger rod 20. The secondary plunger tip 21 and the tip removal rod 22 cannot be used to mix the contents of the chamber 13, e.g., the medication 24. The tip removal rod 22 cannot engage the primary plunger tip 18 when the primary plunger tip 18 is located at the distal end 14 of the chamber 13 of the hollow barrel 11. As such, the user must engage the elongated tip plunger rod 20 to the primary plunger tip 18 to effectively mix the contents of the chamber 13, e.g., the medication 24.

Preferably, the elongated tip plunger rod 20, tip removal rod 22, primary plunger tip 18, and secondary plunger tip 21 can be color coded to aid in the use of the syringe assembly 10. In such an embodiment, the elongated tip plunger rod 20 and the primary plunger tip 18 can have one color, e.g., blue, and the tip removal rod 22 and the secondary plunger tip 21 can have a second color, e.g., red. This color coded scheme can aid the user in only using the elongated tip plunger rod 20 with the primary plunger tip 18 and only using the tip removal rod 22 with the secondary plunger tip 21. Alternatively, the elongated tip plunger rod 20, tip removal rod 22, primary plunger tip 18, and secondary plunger tip 21 can be coded with corresponding numerals, letters or other relevant markings to aid in the use of the syringe assembly 10.

The tip plunger rod 22 can be manufactured from any suitable material. Suitable materials include glass and plastic (e.g., polypropylene, polyethylene, polycarbonate, polystyrene, and the like). The tip plunger rod 22 can be sterilized. The tip plunger rod 22 can be sterilized by any suitable means. More specifically, the tip plunger rod 22 can be sterilized by gamma irradiation. The sterilization can occur before the medication 24 is introduced into the chamber 13 of the hollow barrel 11. Alternatively, sterilization can occur after the medication 24 is introduced into the chamber 13 of the hollow barrel 11.

The syringe assembly 10 can include a medication 24 (i.e., pharmaceutical or drug). The medication 24 can be sterilized. The medication 24 can be sterilized by any suitable means. More specifically, the medication 24 can be sterilized by filtration. The sterilization can occur prior to the introduction of the solution containing the medication 24 into the chamber 13 of the hollow barrel 11 (i.e., prior to lyophilization). The medication 24 can be located between the distal end 14 of the chamber 13 of the hollow barrel 11 and the primary plunger tip 18. Specifically, the medication 24 can be located toward the distal end 14 of the chamber 13 of the hollow barrel 11 such that the medication 24 is in contact with the passageway 16.

Any suitable medication or pharmaceutically acceptable salt thereof can be employed. Suitable classes of pharmaceuticals include antibiotics, peptides, hormones, analgesics, growth factors, vaccines and any agent described in U.S. Pat. No. B1 4,938,763, the disclosure of which is incorporated herein by reference. The drug can exist as a liquid, a solid (e.g., crystal or powder), an oil, or as a clay-like material. The drug can also be a lyophilized medication (e.g., leuprolide acetate or doxycycline), a powdered medication, or a granular medication. In addition, the drug may exist in a microcapsule containing the drug or as a microparticle.

The present invention also provides a process for providing a lyophilized medication (i.e., lyophilizate) in a syringe assembly 10. The process includes providing a syringe assembly 10. The distal end 14 of the hollow barrel 11 or the proximal end 15 of the hollow barrel 11 is sealed and a solution comprising the medication is placed in the chamber 13. The solution is then lyophilized in the chamber 13 to provide a lyophilizate. A primary plunger tip 18, slidably positioned in fluid tight engagement with the interior wall 12, is inserted inside the hollow barrel 11. The primary plunger tip 18 is inserted inside the hollow barrel 11 such that the primary plunger tip 18 is disposed between the lyophilized medication and the proximal end 15 of the hollow barrel 11. Specifically, the primary plunger tip 18 can be positioned toward the distal end 14 of the hollow barrel 11. More specifically, the primary plunger tip 18 can be positioned toward the distal end 14 of the hollow barrel 11 such that the primary plunger tip 18 is in contact with the lyophilized medication (i.e., lyophilizate). a secondary plunger tip 21, slidably positioned in fluid tight engagement with the interior wall 12, is inserted inside the hollow barrel 11. The secondary plunger tip 21 can be engaged to a tip plunger rod 22. The secondary plunger tip 21 can be inserted inside the hollow barrel 11 such that the secondary plunger tip 21 is disposed between the primary plunger tip 18 and the proximal end 15 of the hollow barrel 11. More specifically, the secondary plunger tip 21 can be positioned toward the proximal end 15 of the hollow barrel 11 such that the secondary plunger tip 21 is in contact with the proximal end 15 of the hollow barrel 11.

As used herein, "lyophilization" is the removal of solvent from the frozen state by sublimation. Lyophilization is accomplished by freezing the solution below its melting point and manipulating the temperature and pressure conditions affecting the frozen solution to sublimation. Precise control of these conditions permits drying from the frozen state without product melt-back. In practical applications, the process is accelerated and more precisely controlled under reduced pressure conditions. McGraw-Hill Concise Encyclopedia of Science & Technology, Fourth Edition, Sybil P. Parker, 1997. The vacuum causes the water molecules to "sublimate", i.e., to become gaseous and leave the solid, without going through a liquid state. As used herein, "lyophilizate" is the solid, powder or granular material remaining after lyophilization. The solid, powder or granular material is essentially free of solvent.

The process for providing a lyophilized medication (i.e., lyophilizate) in a syringe assembly 10 can further include the step of packaging the syringe assembly containing the lyophilized medication. The packaging of the syringe assembly 10 typically includes placing the syringe assembly 10 in a pouch and sealing the pouch. The syringe assembly 10 can be placed in a pouch and the pouch can be sealed under sterile conditions. The pouch can be manufactured from any suitable material. Suitable materials include plastic (e.g., polypropylene, polyethylene, polycarbonate, polystyrene, and the like), thermoplastic elastomers, and foil-lined plastics.

The process for providing a lyophilized medication (i.e., lyophilizate) in a syringe assembly 10 can further include the step of applying a label to the syringe assembly 10. The label can be applied to the hollow barrel 11 of the syringe assembly 10. The label can be clear or opaque. The label can include a description of the contents of the syringe assembly 10 (i.e., the medication 24). In addition, the label can include directions for administering the contents of the syringe assembly 10 (i.e., the medication 24).

The process for providing a lyophilized medication (i.e., lyophilizate) in a syringe assembly 10 can further include the step of engaging a flange extender 29 to the proximal end 15 of the hollow barrel 11 of the syringe assembly 10. The flange extender 29 can be engaged to the proximal end 15 of the hollow barrel 11 of the syringe assembly 10. The distal end 14 of hollow barrel 11 can be inserted through the proximal end 58 of aperture 56 of the flange extender 29. The hollow barrel 11 can be inserted through the aperture 56 until the flange extender 29 is in continuous contact with flange 34.

The present invention also provides a process for reconstituting a medication 24 (i.e., lyophilizate) in a syringe assembly 10. The process includes providing a syringe assembly 10 that includes a discharge assembly (e.g., needle 25) engaged to the distal end 14 of the hollow barrel 11. The hollow barrel 11 can contain a medication 24 disposed between the primary plunger tip 18 and the distal end 14 of the hollow barrel 11. The secondary plunger tip 21 is removed from the hollow barrel 11. The distal end 53 of the discharge assembly (e.g., needle 25) is placed in communication with a diluent 60. The primary plunger tip 18 is urged proximally and away from the distal end 14 of the chamber 13 of the hollow barrel 11. The primary plunger tip 18 can be urged proximally and away from the distal end 14 of the chamber 13 of the hollow barrel 11 with the use of an elongated tip plunger rod 20. In such an embodiment, the elongated tip plunger rod 20 is engaged to the primary plunger tip 18 as described above. As the elongated tip plunger rod 20 is urged proximally and away from the distal end 14 of the chamber 13 of the hollow barrel 11, the primary plunger tip 18 is urged proximally and away from the distal end 14 of the chamber 13 of the hollow barrel 11. The diluent 60 is thereby urged through the lumen 54 of the needle, through the distal end 14 of the hollow barrel 11, into the chamber 13 of the hallow barrel 11, and into contact with the medication 24, thereby effectively reconstituting the medication 24. It is also possible and within the confines of the present invention to reconstitute the medication 24 by connecting the distal end 14 of the hollow barrel 11 directly to a liquid reservoir without the use of a discharge assembly (e.g., needle 25).

Alternatively, the distal end of a second syringe assembly can be connected to a third syringe containing a diluent by means of a luer-lock coupler and the diluent can be discharged into the second syringe where it comes in contact with the medication. The mixture of diluent and medication can then be pushed back and forth between the two syringes until the contents are thoroughly mixed. The contents can then be drawn into one of the syringes, the coupler and other syringe can be removed, and a discharge assembly or cannula (e.g., a needle) can be attached to the syringe with the contents.

The diluent 60 can contain any suitable liquid carrier. Suitable liquid carriers include a collagen solution, an oil (e.g., vegetable oil), a sterile aqueous solution, a sterile saline solution, an alcoholic solution, a polymer solution or any suitable mixture thereof. In addition, the liquid carrier can be an emulsion formed from a mixture of an oil (e.g., vegetable oil) and a sterile aqueous solution or a sterile saline solution. Specifically, the liquid polymer solution can be the Atrigel® system.

The syringe assembly 10 of the present invention allows for the reconstitution and/or mixing of a lyophilized material, e.g., pharmaceutical, in a sterile environment. The sterility of the entire surface of the syringe assembly 10 in which the lyophilized material, e.g., pharmaceutical, comes into contact during the reconstitution is maintained during the manufacturing, shipping, and storage of the syringe assembly 10. This includes the surface of the syringe assembly 10 that is located between the plunger tip located on or near the lyophilized material and the proximal end of the syringe assembly 10.

Preferably, the reconstitution of the lyophilized material, e.g., pharmaceutical, can be accomplished via a syringe-to-syringe mixing. In such an embodiment, the sterility of the entire surface of the syringe assembly 10 in which the lyophilized material comes into contact during the reconstitution is maintained. The sterility is maintained during the manufacturing, shipping, and storage of the syringe assembly 10, as well as during the reconstitution (e.g., syringe-to-syringe) of the lyophilized material.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A syringe assembly comprising:
   a hollow barrel having an uniform interior wall defining a chamber for retaining medication, wherein the hollow barrel comprises a distal end and a proximal end, wherein the distal end of the hollow barrel has a passageway therethrough communicating with the chamber and the proximal end of the hollow barrel has an aperture therethrough;
   a primary plunger tip having a proximal end and a distal end slidably positioned in fluid tight engagement with the uniform interior wall wherein the proximal end of the primary plunger tip has a receptor to engage an engager on the distal end of an elongated tip plunger rod;
   a secondary plunger tip having a proximal end and a distal end slidably positioned in fluid tight engagement with the uniform interior wall, wherein the proximal end of the secondary plunger tip has a receptor to engage an engager on the distal end of a tip removal rod, wherein the secondary plunger tip is disposed between the primary plunger tip and the proximal end of the hollow barrel; and
   the tip removal rod having the engager located on the distal end of the tip removal rod, the engager being configured to engage the receptor of the secondary plunger tip to facilitate operation of the secondary plunger tip.

2. The syringe assembly of claim 1 wherein the distal end of the hollow barrel is configured to engage at least one of a discharge assembly and a sealing cap.

3. The syringe assembly of claim 2 wherein the discharge assembly includes a needle.

4. The syringe assembly of claim 1 further comprising a sealing cap positioned at the distal end of the hollow barrel, wherein the sealing cap seals the passageway from contamination.

5. The syringe assembly of claim 1, wherein the elongated tip plunger rod comprises the engager located on the distal end, the engager being configured to engage the receptor of the primary plunger tip-, to facilitate operation of the primary plunger tip.

6. The syringe assembly of claim 1 further comprising a medication disposed between the primary plunger tip and the distal end of the hollow barrel.

7. The syringe assembly of claim 6 wherein the medication is selected from lyophilized medication, powdered medication, and granular medication.

8. The syringe assembly of claim 7 wherein the lyophilized medication is leuprolide acetate.

9. The syringe assembly of claim 1 further comprising a flange extender projecting radially outward from the proximal end of the hollow barrel.

10. The syringe assembly of claim 1 wherein at least one of the primary plunger tip and the secondary plunger tip comprises a plurality of annular ribs dimensioned for sliding fluid-tight engagement with the interior wall.

11. The syringe assembly of claim 1 wherein the hollow barrel is made from material selected from glass and plastic.

12. The syringe assembly of claim 1 wherein at least one of the primary plunger tip and the secondary plunger tip is made from material selected from natural rubber, synthetic rubber and thermoplastic elastomers.

13. A process for providing a lyophilized medication in a syringe assembly, the process comprising:
   providing a hollow barrel having an interior wall defining a chamber for retaining a solution comprising a medication, wherein the hollow barrel comprises a distal end and a proximal end, wherein the distal end of the hollow barrel has a passageway therethrough communicating with the chamber and the proximal end of the hollow barrel has an aperture therethrough, wherein the distal end of the hollow barrel or the proximal end of the hollow barrel is sealed;

placing a solution comprising the medication in the chamber;

lyophilizing the solution in the chamber to provide a lyophilized medication;

inserting a primary plunger tip having a proximal end and a distal end that is slidably positioned in fluid tight engagement with the interior wall, wherein the primary plunger tip has a receptor on the proximal end of the primary plunger tip to engage an engager on the distal end of an elongated tip plunger rod, wherein the primary plunger tip is disposed between the lyophilized medication and the proximal end of the hollow barrel; and inserting a secondary plunger tip having a proximal end and a distal end that is slidably positioned in fluid tight engagement with the interior wall, wherein the secondary plunger tip has a receptor on the proximal end that is engaged to an engager on the distal end of a tip removal rod, wherein the secondary plunger tip is disposed between the primary plunger tip and the proximal end of the hollow barrel, to provide a lyophilized medication in a syringe assembly.

14. The process of claim 13 wherein the distal end of the hollow barrel is configured to engage at least one of a discharge assembly and a sealing cap.

15. The process of claim 14 wherein the discharge assembly includes a needle.

16. The process of claim 13 wherein the medication is leuprolide acetate.

17. The process of claim 13 wherein at least one of the primary plunger tip and the secondary plunger tip comprises a plurality of annular ribs dimensioned for sliding fluid-tight engagement with the hollow barrel.

18. The process of claim 13 wherein the hollow barrel is made from material selected from glass and plastic.

19. The process of claim 13 wherein at least one of the primary plunger tip and the secondary plunger tip is made from material selected from natural rubber, synthetic rubber and thermoplastic elastomers.

20. The process of claim 13 wherein the medication is sterilized by filtration.

21. The process of claim 13 wherein at least one of the hollow barrel, primary plunger tip, and the secondary plunger tip is sterilized by gamma irradiation.

22. The process of claim 13 further including the step of packaging the syringe assembly containing the lyophilized medication.

23. The process of claim 22 wherein the packaging is under sterile conditions.

24. The process of claim 13 further including the step of labeling the syringe assembly containing the lyophilized medication.

25. The process of claim 13 further including the step of engaging a flange extender to the proximal end of the hollow barrel of the syringe assembly, wherein the flange extender projects radially outward from the proximal end of the hollow barrel of the syringe assembly.

26. A process for reconstituting a medication in a syringe, the process comprising:

providing a syringe assembly with medication according to claim 6;

removing the secondary plunger tip from the hollow barrel; placing the discharge assembly in communication with a diluent; and urging the primary plunger tip proximally and away from the distal end of the hollow barrel, thereby urging the diluent through the discharge assembly and through the distal end of the hollow barrel, thereby contacting the medication and effectively reconstituting the medication.

27. The process of claim 26 wherein the distal end of the hollow barrel is configured to engage at least one of a discharge assembly and a sealing cap.

28. The process of claim 26 wherein the discharge assembly includes a needle.

29. The process of claim 26 wherein the medication is selected from lyophilized medication, powdered medication, and granular medication.

30. The process of claim 29 wherein the lyophilized medication is leuprolide acetate.

31. The process of claim 26 wherein the urging the primary plunger tip proximally and away from the distal end of the hollow barrel is accomplished by engaging the primary plunger tip with an elongated tip plunger rod and urging the elongated tip plunger rod proximally and away from the distal end of the hollow barrel, thereby urging the diluent through the distal end of the hollow barrel and into the chamber, thereby effectively reconstituting the medication.

32. The process of claim 26 wherein at least one of the primary plunger tip and the secondary plunger tip comprises a plurality of annular ribs dimensioned for sliding fluid-tight engagement with the hollow barrel.

33. The process of claim 26 wherein the hollow barrel is made from material selected from glass and plastic.

34. The process of claim 26 wherein at least one of the primary plunger tip and the secondary plunger tip is made from material selected from natural rubber, synthetic rubber and thermoplastic elastomers.

35. The process of claim 26 wherein the medication is sterilized by filtration.

36. The process of claim 26 wherein at least one of the hollow barrel, primary plunger tip, and the secondary plunger tip is sterilized by gamma irradiation.

* * * * *